United States Patent
Maseda et al.

(10) Patent No.: US 8,834,352 B2
(45) Date of Patent: Sep. 16, 2014

(54) ENDOSCOPE WORKING CHANNEL WITH MULTIPLE FUNCTIONALITY

(75) Inventors: Luis J. Maseda, Natick, MA (US); Barry Weitzner, Acton, MA (US); Roy H. Sullivan, Millville, MA (US); William Lucas Churchill, Bolton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 761 days.

(21) Appl. No.: 13/037,537

(22) Filed: Mar. 1, 2011

(65) Prior Publication Data

US 2011/0213202 A1 Sep. 1, 2011

Related U.S. Application Data

(63) Continuation of application No. 11/386,861, filed on Mar. 22, 2006, now Pat. No. 7,918,783.

(51) Int. Cl.
*A61B 1/00* (2006.01)
*A61B 1/04* (2006.01)
*A61B 17/29* (2006.01)

(52) U.S. Cl.
CPC ......... *A61B 1/108* (2013.01); *A61B 2017/2901* (2013.01); *A61B 2017/293* (2013.01)
USPC .............................. 600/104; 600/128; 600/130

(58) Field of Classification Search
CPC . A61B 1/00087; A61B 1/00234; A61B 1/018
USPC ................................ 600/104, 117, 128, 137; 604/167.01–167.06
See application file for complete search history.

(56) References Cited

U.S. PATENT DOCUMENTS

| | | |
|---|---|---|
| 1,127,948 A | 2/1915 | Wappler |
| 2,036,528 A | 4/1936 | Kesling |
| 2,950,609 A | 8/1960 | Goodloe |
| 3,554,192 A | 1/1971 | Isberner |
| 3,805,770 A | 4/1974 | Okada |
| 3,895,636 A | 7/1975 | Schmidt |
| 3,955,578 A | 5/1976 | Chamness et al. |
| 4,046,150 A | 9/1977 | Schwartz et al. |
| 4,256,113 A | 3/1981 | Chamness |
| 4,294,254 A | 10/1981 | Chamness |
| 4,326,530 A | 4/1982 | Fleury, Jr. |
| 4,327,711 A | 5/1982 | Takagi |

(Continued)

FOREIGN PATENT DOCUMENTS

| | | |
|---|---|---|
| DE | 28 29 159 A1 | 1/1980 |
| DE | 36 16 193 A1 | 11/1986 |

(Continued)

OTHER PUBLICATIONS

Product Brochure, "TRIO 14, Re-Engineering Over-The-Wire Balloon Technology," 4 pages, 1994.

*Primary Examiner* — Alireza Nia
(74) *Attorney, Agent, or Firm* — Bookoff McAndrews, PLLC

(57) ABSTRACT

Endoscopic instrument assemblies and methods for making and using the same. An example endoscopic instrument assembly includes an endoscope having a working channel and an endoscopic instrument slidably disposed in the working channel. The inside surface of the working channel and the outside surface of the endoscopic instrument each have a non-circular cross-sectional shape along at least a portion of their respective lengths.

20 Claims, 5 Drawing Sheets

(56) References Cited

U.S. PATENT DOCUMENTS

| | | | |
|---|---|---|---|
| 4,345,599 A | 8/1982 | McCarrell |
| 4,430,083 A | 2/1984 | Ganz et al. |
| 4,436,087 A | 3/1984 | Ouchi |
| 4,493,320 A | 1/1985 | Treat |
| 4,503,855 A | 3/1985 | Maslanka |
| 4,590,938 A | 5/1986 | Segura et al. |
| 4,593,680 A | 6/1986 | Kubokawa |
| 4,607,619 A | 8/1986 | Seike et al. |
| 4,619,260 A | 10/1986 | Magill et al. |
| 4,632,110 A | 12/1986 | Sanagi |
| 4,682,981 A | 7/1987 | Suzuki et al. |
| 4,706,656 A | 11/1987 | Kuboto |
| 4,742,817 A | 5/1988 | Kawashima et al. |
| 4,763,668 A | 8/1988 | Macek et al. |
| 4,785,825 A | 11/1988 | Romaniuk et al. |
| 4,790,831 A | 12/1988 | Skribiski |
| D301,614 S | 6/1989 | Kozak et al. |
| 4,840,176 A | 6/1989 | Ohno |
| 4,840,623 A | 6/1989 | Quackenbush |
| 4,841,949 A | 6/1989 | Shimizu et al. |
| 4,852,550 A | 8/1989 | Koller et al. |
| 4,869,238 A | 9/1989 | Opie et al. |
| 4,872,456 A | 10/1989 | Hasson |
| 4,874,371 A | 10/1989 | Comben et al. |
| 4,905,691 A | 3/1990 | Rydell |
| 4,945,920 A | 8/1990 | Clossick |
| 4,950,232 A | 8/1990 | Ruzicka et al. |
| 4,967,732 A | 11/1990 | Inoue |
| 4,973,321 A | 11/1990 | Michelson |
| 5,005,755 A | 4/1991 | Takahashi et al. |
| 5,026,371 A | 6/1991 | Rydell et al. |
| 5,059,199 A | 10/1991 | Okada et al. |
| 5,066,295 A | 11/1991 | Kozak et al. |
| 5,084,054 A | 1/1992 | Bencini et al. |
| 5,088,819 A | 2/1992 | Storz |
| 5,114,403 A | 5/1992 | Clarke et al. |
| 5,125,909 A | 6/1992 | Heimberger |
| 5,129,913 A | 7/1992 | Ruppert |
| 5,133,727 A | 7/1992 | Bales et al. |
| 5,147,316 A | 9/1992 | Castillenti |
| 5,147,373 A | 9/1992 | Ferzli |
| RE34,110 E | 10/1992 | Opie et al. |
| 5,156,590 A | 10/1992 | Vilmar |
| 5,158,561 A | 10/1992 | Rydell et al. |
| 5,163,942 A | 11/1992 | Rydell |
| 5,176,677 A | 1/1993 | Wuchinich |
| 5,176,702 A | 1/1993 | Bales et al. |
| 5,179,935 A | 1/1993 | Miyagi |
| 5,183,470 A | 2/1993 | Wettermann |
| 5,184,602 A | 2/1993 | Anapliotis et al. |
| 5,201,740 A | 4/1993 | Nakao et al. |
| 5,201,743 A | 4/1993 | Haber et al. |
| 5,213,093 A | 5/1993 | Swindle |
| 5,228,451 A | 7/1993 | Bales et al. |
| 5,244,619 A | 9/1993 | Burnham |
| 5,254,117 A | 10/1993 | Rigby et al. |
| 5,254,130 A | 10/1993 | Poncet et al. |
| 5,279,280 A | 1/1994 | Bacich et al. |
| 5,281,220 A | 1/1994 | Blake, III |
| 5,281,230 A | 1/1994 | Heidmueller |
| 5,290,294 A | 3/1994 | Cox et al. |
| 5,318,564 A | 6/1994 | Eggers |
| 5,334,169 A | 8/1994 | Brown et al. |
| 5,336,227 A | 8/1994 | Nakao et al. |
| 5,358,493 A | 10/1994 | Schweich, Jr. et al. |
| 5,366,443 A | 11/1994 | Eggers et al. |
| 5,373,840 A | 12/1994 | Knighton |
| 5,376,094 A | 12/1994 | Kline |
| 5,394,885 A | 3/1995 | Francese |
| 5,403,342 A | 4/1995 | Tovey et al. |
| 5,404,887 A | 4/1995 | Prather |
| 5,406,939 A | 4/1995 | Bala |
| 5,439,478 A | 8/1995 | Palmer |
| 5,465,710 A | 11/1995 | Miyagi et al. |
| 5,486,182 A | 1/1996 | Nakao et al. |
| 5,496,292 A | 3/1996 | Burnham |
| 5,501,692 A | 3/1996 | Riza |
| 5,507,296 A | 4/1996 | Bales et al. |
| 5,542,948 A | 8/1996 | Weaver et al. |
| 5,582,617 A | 12/1996 | Klieman et al. |
| 5,584,843 A | 12/1996 | Wulfman et al. |
| 5,588,964 A | 12/1996 | Imran et al. |
| 5,591,202 A | 1/1997 | Slater et al. |
| 5,601,533 A | 2/1997 | Hancke et al. |
| 5,607,404 A | 3/1997 | Khairkhahan |
| 5,636,634 A | 6/1997 | Kordis et al. |
| 5,642,736 A | 7/1997 | Avitall |
| 5,647,846 A | 7/1997 | Berg et al. |
| 5,666,965 A | 9/1997 | Bales et al. |
| 5,681,296 A | 10/1997 | Ishida |
| 5,685,822 A | 11/1997 | Harhen |
| 5,685,853 A | 11/1997 | Bonnet |
| 5,707,392 A | 1/1998 | Kortenbach |
| 5,718,360 A | 2/1998 | Green et al. |
| 5,728,148 A | 3/1998 | Bostrom et al. |
| 5,738,630 A | 4/1998 | Suzuki et al. |
| 5,741,271 A | 4/1998 | Nakao et al. |
| 5,746,747 A | 5/1998 | McKeating |
| 5,755,724 A | 5/1998 | Yoon |
| 5,759,187 A | 6/1998 | Nakao et al. |
| 5,762,631 A | 6/1998 | Klein |
| 5,766,217 A | 6/1998 | Christy |
| 5,769,841 A | 6/1998 | Odell et al. |
| 5,785,689 A | 7/1998 | de Toledo et al. |
| 5,792,116 A | 8/1998 | Berg et al. |
| 5,800,444 A | 9/1998 | Ridinger et al. |
| 5,810,802 A | 9/1998 | Panescu et al. |
| 5,814,052 A | 9/1998 | Nakao et al. |
| 5,817,111 A | 10/1998 | Riza |
| 5,820,464 A | 10/1998 | Parlato |
| 5,820,546 A | 10/1998 | Ouchi |
| 5,827,177 A | 10/1998 | Oneda et al. |
| 5,827,272 A | 10/1998 | Breining et al. |
| 5,846,248 A | 12/1998 | Chu et al. |
| 5,860,975 A | 1/1999 | Goble et al. |
| 5,882,347 A | 3/1999 | Mouris-Laan et al. |
| 5,885,508 A | 3/1999 | Ishida |
| 5,901,621 A | 5/1999 | Chen |
| 5,906,620 A | 5/1999 | Nakao et al. |
| 5,906,621 A | 5/1999 | Secrest et al. |
| 5,931,849 A | 8/1999 | Desvignes et al. |
| 5,951,579 A | 9/1999 | Dykes |
| 5,954,635 A | 9/1999 | Foley et al. |
| 5,954,731 A | 9/1999 | Yoon |
| 5,957,932 A | 9/1999 | Bates et al. |
| 5,961,511 A | 10/1999 | Mortier et al. |
| 5,971,994 A | 10/1999 | Fritzsch |
| 5,976,130 A | 11/1999 | McBrayer et al. |
| 5,980,519 A | 11/1999 | Hahnen et al. |
| 5,984,904 A | 11/1999 | Steen et al. |
| 5,984,920 A | 11/1999 | Steinbach |
| 5,989,247 A | 11/1999 | Chambers |
| 5,993,474 A | 11/1999 | Ouchi |
| 6,001,096 A | 12/1999 | Bissinger et al. |
| 6,007,560 A | 12/1999 | Gottlieb et al. |
| 6,010,512 A | 1/2000 | Chu et al. |
| 6,015,381 A | 1/2000 | Ouchi |
| 6,015,415 A | 1/2000 | Avellanet |
| 6,017,358 A | 1/2000 | Yoon et al. |
| 6,019,758 A | 2/2000 | Slater |
| 6,024,708 A | 2/2000 | Bales et al. |
| 6,027,460 A | 2/2000 | Shturman |
| 6,041,679 A | 3/2000 | Slater et al. |
| 6,042,553 A | 3/2000 | Solar et al. |
| 6,050,995 A | 4/2000 | Durgin |
| 6,068,603 A | 5/2000 | Suzuki |
| 6,071,233 A | 6/2000 | Ishikawa et al. |
| 6,074,408 A | 6/2000 | Freeman |
| 6,086,600 A | 7/2000 | Kortenbach |
| 6,090,073 A | 7/2000 | Gill |
| 6,090,108 A | 7/2000 | McBrayer et al. |
| 6,090,129 A | 7/2000 | Ouchi |
| 6,093,195 A | 7/2000 | Ouchi |
| 6,099,483 A | 8/2000 | Palmer et al. |

(56) References Cited

U.S. PATENT DOCUMENTS

| | | |
|---|---|---|
| 6,099,505 A | 8/2000 | Ryan et al. |
| 6,123,678 A | 9/2000 | Palmer et al. |
| 6,142,956 A | 11/2000 | Kortenbach et al. |
| 6,168,571 B1 | 1/2001 | Solar et al. |
| 6,174,292 B1 | 1/2001 | Kortenbach et al. |
| 6,193,671 B1 | 2/2001 | Turturro et al. |
| 6,224,611 B1 | 5/2001 | Ouchi |
| 6,235,026 B1 | 5/2001 | Smith |
| 6,299,612 B1 | 10/2001 | Ouchi |
| 6,409,727 B1 | 6/2002 | Bales et al. |
| 6,454,702 B1 | 9/2002 | Smith |
| 6,471,639 B2 | 10/2002 | Rudischhauser et al. |
| 6,517,539 B1 | 2/2003 | Smith et al. |
| 6,537,205 B1 | 3/2003 | Smith |
| 6,589,251 B2 * | 7/2003 | Yee et al. .................. 606/108 |
| 6,629,630 B2 | 10/2003 | Adams |
| 6,645,140 B2 | 11/2003 | Brommersma |
| 6,761,717 B2 | 7/2004 | Bales et al. |
| 6,817,973 B2 | 11/2004 | Merril et al. |
| 6,824,544 B2 | 11/2004 | Boebel et al. |
| 6,840,900 B2 | 1/2005 | Smith |
| 6,881,186 B2 | 4/2005 | Smith |
| 6,972,017 B2 | 12/2005 | Smith et al. |
| 7,029,435 B2 | 4/2006 | Nakao |
| 7,033,315 B2 | 4/2006 | Smith |
| 7,749,156 B2 * | 7/2010 | Ouchi .......................... 600/104 |
| 2003/0045768 A1 | 3/2003 | Hirooka et al. |
| 2004/0087892 A1 | 5/2004 | Cunningham |
| 2005/0107668 A1 | 5/2005 | Smith |
| 2006/0178658 A1 | 8/2006 | Smith |

FOREIGN PATENT DOCUMENTS

| | | |
|---|---|---|
| DE | 94 18 834.3 U | 3/1995 |
| DE | 199 53 359 A1 | 5/2000 |
| EP | 0 943 292 A1 | 9/1999 |
| EP | 1481628 A1 | 12/2004 |
| JP | 2002-51974 | 2/2002 |
| JP | 2003-235791 A | 8/2003 |
| WO | WO 92/22254 A1 | 12/1992 |
| WO | WO 99/07288 | 2/1999 |
| WO | WO 00/42926 | 7/2000 |
| WO | WO 00/53107 | 9/2000 |
| WO | WO 01/10321 | 2/2001 |
| WO | WO 2005/081202 A1 | 9/2005 |

\* cited by examiner

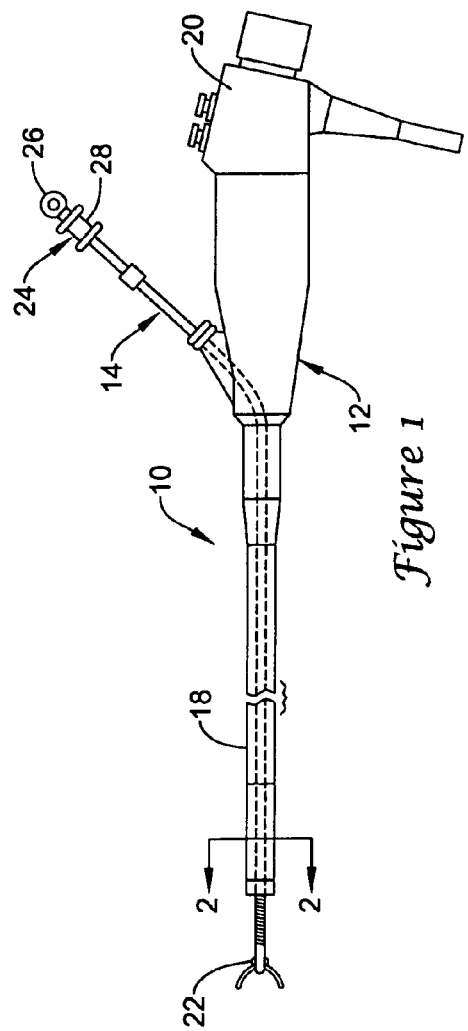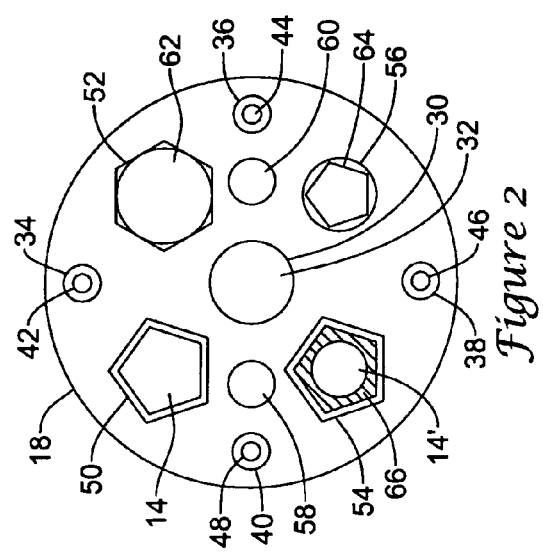

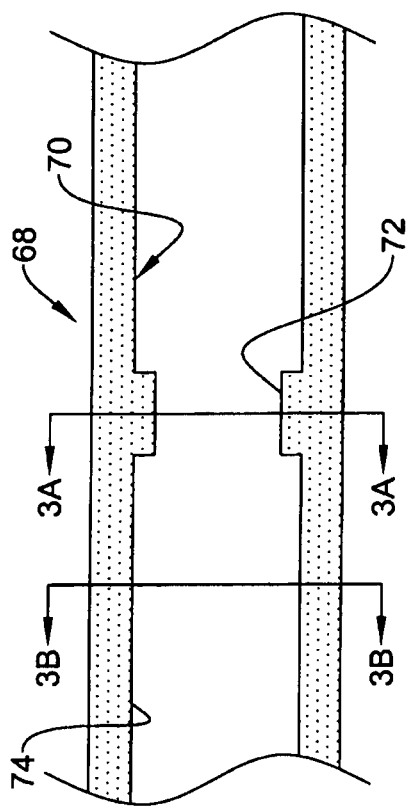

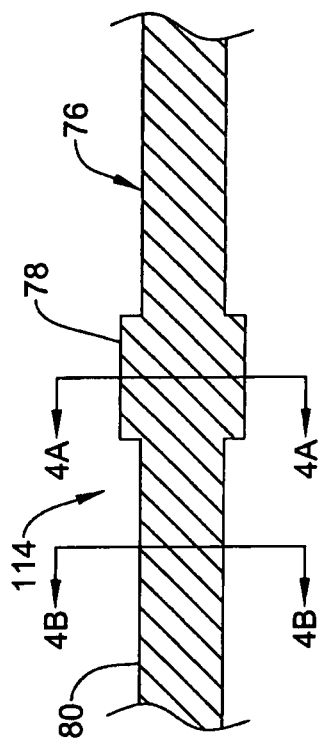
*Figure 4*
*Figure 4A*
*Figure 4B*

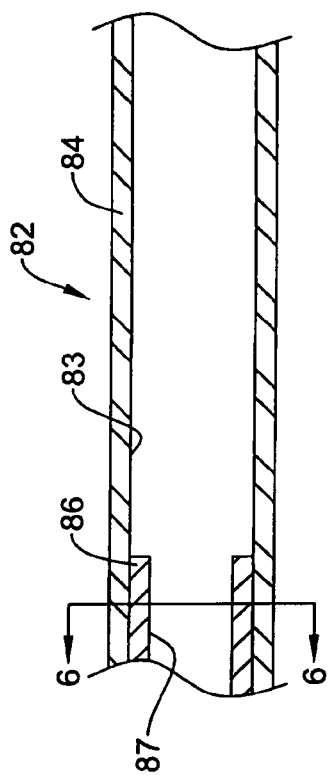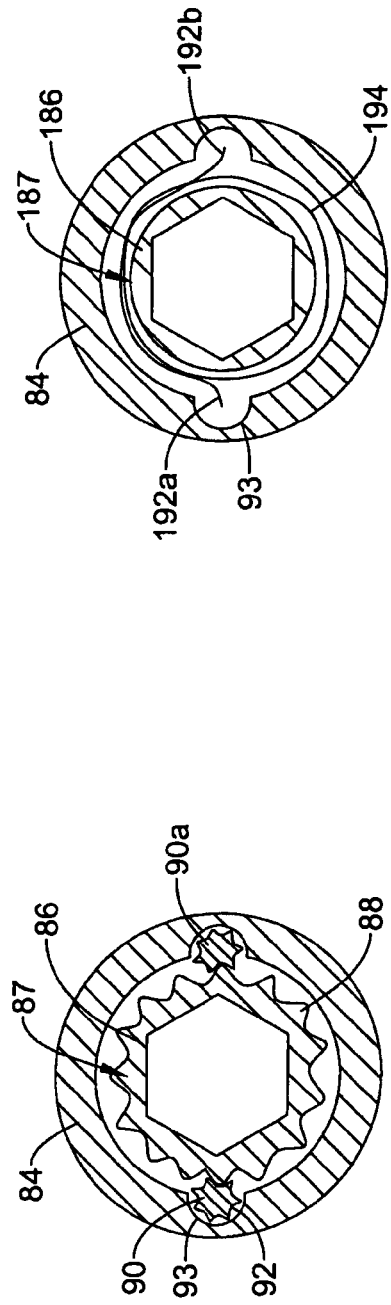

ENDOSCOPE WORKING CHANNEL WITH MULTIPLE FUNCTIONALITY

CROSS-REFERENCE TO RELATED APPLICATION

This application is a continuation of U.S. application Ser. No. 11/386,861, filed Mar. 22, 2006 (now U.S. Pat. No. 7,918,783), which is incorporated herein by reference in its entirety.

FIELD OF THE INVENTION

This invention pertains broadly to surgical instruments. More particularly, this invention pertains to an endoscope and endoscopic instruments that are disposed in a working channel of the endoscope.

BACKGROUND

A wide variety of medical devices have been developed for medical use, for example, endoscopic and/or surgical use. Some of these devices include endoscopes, endoscopic instruments, and other related devices that have certain characteristics. Of the known medical devices, each has certain advantages and disadvantages. There is an ongoing need to provide alternative designs and methods of making and using medical devices.

BRIEF SUMMARY

The invention provides design, material, and manufacturing method alternatives for medical devices, for example, endoscopes, endoscopic instruments, and endoscopic instrument assemblies. An example endoscopic instrument assembly includes an endoscope having a working channel and an endoscopic instrument slidably disposed in the working channel. The inside surface of the working channel and the outside surface of the endoscopic instrument each have a non-circular cross-sectional shape along at least a portion of their respective lengths. Methods for making and using medical devices including endoscopic instrument assemblies are also disclosed. Some of these and other features and characteristics of the inventive devices and methods are described in more detail below.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1 is side view of an example endoscopic instrument assembly;

FIG. 2 is a cross-section across line 2-2 in FIG. 1;

FIG. 3 is a cross-sectional view of an example working channel;

FIG. 3A is a cross-section across line 3A-3A in FIG. 3;

FIG. 3B is a cross-section across line 3B-3B in FIG. 3;

FIG. 4 is a side view of a portion of an example endoscopic instrument;

FIG. 4A is a cross-section across line 4A-4A in FIG. 4;

FIG. 4B is a cross-section across line 4B-4B in FIG. 4;

FIG. 5 is a cross-sectional view of another example working channel;

FIG. 6 is a cross-section across line 6-6 in FIG. 5;

FIG. 7 is an alternative example cross-section taken across line 6-6 in FIG. 5;

DETAILED DESCRIPTION

Figure 9:
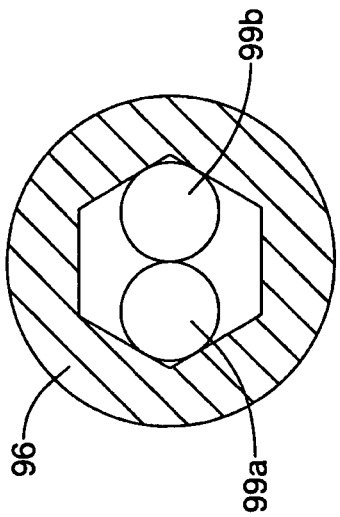
FIG. 9 is a cross-sectional view of the working channel shown in FIG. 8 having a plurality of different instruments disposed therein.

The following description should be read with reference to the drawings wherein like reference numerals indicate like elements throughout the several views. The detailed description and drawings illustrate example embodiments of the claimed invention.

FIG. 1 illustrates an example endoscopic instrument assembly 10. Assembly 10 includes an endoscope 12 and an endoscopic instrument 14 disposed in a working channel (not shown in FIG. 1, see FIG. 2 for example working channels) defined in endoscope 12. Endoscope 12 includes an elongate tubular portion 18 and a proximal handle portion 20 adapted to manipulate and direct the distal end of tubular portion 18.

Endoscopic instrument 14 may include an end effector 22 and one or more control members 24 that may manipulate or otherwise control end effector 22. In some embodiments, end effector 22 may be a biopsy forceps or linkage mechanism as depicted in FIG. 1. Alternatively, end effector 22 may be a snare loop, scissors, punch, needle, and the like, or any other suitable device. Control member 24 may include a thumb ring 26 and a displaceable spool 28, which can be used to manipulate and/or actuate end effector 22. Some additional details regarding suitable types of end effectors and control members (which can also be described as or take the form of handles) can be found in U.S. Pat. Nos. 6,537,205; 6,840,900; 6,454,702; 6,881,186; 6,235,026; and 6,517,539, the entire disclosures of which are incorporated herein by reference.

FIG. 2 is a cross-sectional view of tubular portion 18 of endoscope 12. Here it can be seen that tubular portion 18 may include one or more channels. One or more of these channels, for example channel 30, may be provided for receiving an optical scope or camera device 32 (which may be built therein). A number of additional lumens 34/36/38/40 may be included for receiving control wires 42/44/46/48 that may extend from the handle portion 20 through the tubular portion 18. One or more working channels 50/52/54/56 may also be provided for receiving endoscopic instruments, for example endoscopic instrument 14, therethrough. Other lumens 58/60 may be provided for other purposes. Some additional details regarding endoscopes are described in general in U.S. Pat. No. 5,179,935 to Miyagi, which is incorporated herein by reference in its entirety. It should be noted that tubular portion 18 could also be a tubular medical device other than an endoscope, such as a catheter or guiding tube that includes any number of the features and characteristics of similar devices disclosed herein. Therefore, to the extent applicable, discussion found below relating to channels and instruments may also be applicable to tubular medical devices such as catheters or guiding tubes that include one, two, three or more lumens or channels that are configured to accommodate instruments.

Working channel 52, as depicted in FIG. 2, has a non-circular cross-sectional shape. In this example, the cross-sectional shape is that of a six-sided polygon (i.e., a hexagon). It can be appreciated that a number of alternative shapes may be utilized without departing from the spirit of the invention. For example, the cross-sectional shape may resemble a three, four, five, six, seven, eight, nine, ten, or more sided polygon. The polygon may be regular (i.e., all sides having the same length and all angles between the sides being equal) or irregular. In addition, any other suitable "non-polygonal" shape may be utilized including partially circular shapes, irregular shapes, random shapes, other geometric shapes, or any other suitable shape. Other configurations may include a screw thread or helical ridge or groove formed in channel 52. It should be noted that a vast variety of shapes are contemplated for working channel 52 as well as other channels and instruments disclosed herein.

An endoscopic instrument 62 is disposed in channel 52. Instrument 62 has a generally circular cross-sectional shape. The differences between the shape of channel 52 and instrument 62 may be desirable for a number of reasons. For example, because of the differences in the shape, the blank or vacant space between channel 52 and instrument 62 may allow for fluids to be infused or aspirated through channel 52 while instrument 62 is in place. In some instances, a secondary device (e.g., a needle, guidewire, etc.) may also be disposed in channel 56 adjacent instrument 62. The converse of working channel 52 and instrument 62 is working channel 56 and endoscopic instrument 64. Here, channel 56 has a generally circular cross-sectional shape while instrument 64 has a non-circular cross-sectional shape. This arrangement may be desirable for similar reasons as the arrangement of channel 52 and instrument 62.

In addition, the differences in shape between channels 52/56 and instruments 62/64 may also reduce the surface area in which channels 52/56 and instruments 62/64 are in contact. Reducing surface area contact or otherwise providing space between the working channel and the endoscopic instrument may reduce "backlash" (also known as "whip"). Backlash is understood to be a phenomenon where rotation or other manipulations of an instrument (e.g. instruments 62/64) on one end is not immediately translated to the other end of the instrument until, after a certain amount of un-translated motion occurs, the instrument abruptly translates the motion and/or otherwise "whips" around to catch up with the motion.

Channel 50 is similar to channel 52 in that it has a non-circular cross-sectional shape. Unlike channel 52, however, is that endoscopic instrument 14 disposed in channel 50 also has a non-circular cross-sectional shape. The shapes of channel 50 and instrument 14 are, thus, complementary, i.e., the inner surface of working channel 50 has an inner perimeter and the outer surface of endoscopic instrument 14 has an outer perimeter, and the inner perimeter and the outer perimeter are substantially equal. The complementary shapes allow instrument 14 to fit within channel 50 much like how a key fits in a lock.

Utilizing a "lock-and-key" relationship between channel 50 and instrument 14 may be desirable for a number of reasons. For example, using complementary shapes allows the user to keep track of the orientation of instrument 14 within channel 50. This may be particularly useful when the endoscopic intervention depends on instrument 14 having a particular orientation and/or when it is helpful to the clinician to know what orientation instrument 14 is in at any given time. For example, it may be useful for a clinician to know whether a particular end effector 22 (e.g., a biopsy forceps) is "right-side-up" or "upside-down" prior to attempting to actuate the end effector 22. To further aid this orientation capability, instrument 14 may also include a visual indicia of origin (not shown) such as a colored marker or image that indicates the orientation of instrument 14. Of course, a number of alternative indicia of origin may also be used without departing from the spirit of the invention.

Instrument 14' is disposed in channel 54 and is similar to instrument 14 except that the cross-sectional shape of instrument 14' is defined by a sleeve or coating 66 disposed on the outer surface of instrument 14'. Sleeve 66 allows an otherwise round instrument 14' to utilize the lock-and-key relationship described above and take advantage of its desirable properties.

Sleeve 66 may include a number of different materials. For example, sleeve 66 may comprise a polymer such as polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments, lubricious polymers (including those listed above such as polytetrafluoroethylene) may desirably improve the ability for instrument 14' to move within channel 54. Moreover, because increased lubricity may be desirable, sleeve 66 can also be applied to the outer surface of instrument 14 or any other instrument having a non-circular cross-sectional shape. Sleeves or lubricious coatings may also be utilized for channels and other instruments described herein so that these instruments may more easily move within these channels.

Endoscopic instrument assembly 10 may be used by disposing tubular portion 18 within a body lumen. For example, for an endoscopic procedure that accesses the stomach, tubular portion 18 may extend through the mouth of a patient, down through the esophagus, and into the stomach. Once positioned, instrument 14 (or any other instrument described herein) can extend through the appropriate working channel and into the body lumen. Inside the body lumen, the instrument may be actuated so as to perform its intended intervention.

It is once again useful to consider that a number of different cross-sectional shapes are contemplated for the various working channels and endoscopic instruments described herein. For example, a number of different polygons (e.g., one, two, three, four, five, six, seven, eight, nine, or more sided), partially rounded, irregular, geometric, non-geometric, or other shapes can be used for any of the channels or instruments without departing from the spirit of the invention. It is worth noting that a cross-sectional shape may be described as an inner or outer diameter, an inner or outer perimeter, or by any other suitable designation. To the extent applicable, these descriptions can be used interchangeably.

In some embodiments, the non-circular cross-sectional shape of working channels 50/52/54 and instruments 14/14'/64 extend the full length of each given device. However, this need not be the case. For example, FIG. 3 illustrates a cross-section of another example working channel 68 that has an inner surface 70 with a first region 72 having a non-circular cross-sectional shape and a second region 74 with a generally circular cross-sectional shape. A transverse cross-sectional representation of first region 72 is depicted in FIG. 3A and a transverse cross-sectional representation of second region 74 is depicted in FIG. 3B. Analogously, FIG. 4 illustrates a side view of another example endoscopic instrument 114 that has an outer surface 76 with a first region 78 having a non-circular cross-sectional shape and a second region 80 with a generally circular cross-sectional shape. A transverse cross-sectional representation of first region 78 is depicted in FIG. 4A and a transverse cross-sectional representation of second region 80 is depicted in FIG. 4B.

Instrument 114 and channel 68 may be used together or with any other suitable partner. When used together, it can be appreciated that when non-circular first region 78 of instrument 114 engages non-circular first region 72 of channel 68, instrument 114 "keys" channel 68. Conversely, when first region 78 of instrument 114 is disposed adjacent second region 74 of channel 68, instrument 114 can be more easily rotated within channel 68. The combination of these design features allows the clinician to take advantage of the desirable properties of both circular and non-circular devices by simply shifting the longitudinal position of instrument 114 relative to channel 68.

Designs like these that utilize a non-circular cross-sectional shape along only a portion of the length may provide the endoscopic assembly with a number of desirable features. For example, because a substantial portion of the length of channel 68 and/or instrument 114 have a generally circular cross-sectional shape, non-circular first regions 72/78, when not engaged with one-another, may have reduced surface area contact with circular second regions 74/80. This relationship can reduce backlash and allow for fluid infusion and/or aspiration. Similarly, when non-circular first regions 72/78 are engaged with one another, they may desirably have improved orientation compatibility and otherwise take advantage of the desirable benefits of the "lock-and-key" arrangement.

The length, number, position, and shape of first regions 72/78 can vary in a number of different embodiments. For example, non-circular first regions 72/78 can span any portion of the length of either channel 68 or instrument 114. Likewise, differing embodiments of channel 68 and instrument 114 may include one, two, three, four, or more first regions 72/78. In addition, the various non-circular first regions 72/78 can be positioned at essentially any longitudinal position along channel 68 and instrument 114. For example, FIGS. 3 and 4 illustrate first regions 72/78 being positioned away from the ends of channel 68 and instrument 114. However, this need not be the case as numerous embodiments are contemplated that position first regions 72/78 adjacent the proximal end, distal end, or both of channel 68 and instrument 114, respectively. Similarly, the shape of first regions 72/78 can vary to be any useful shape.

FIG. 5 illustrates another example channel 82 that is similar to other channels described herein. Channel 82 includes an inner surface 83 having a section 84 with a generally circular cross-sectional shape and another section 86 having a non-circular cross-sectional shape. Section 86 may include a rotatable member 87 that is rotatable within section 84 as best seen in FIG. 6. Here it can be seen that rotatable member 87 includes a plurality of teeth or gears 88. A control member or rod 90 having a gear 92 can be extended through an opening 93 in section 84 and into engagement with teeth 88. Rod 90 extends proximally to a position accessible by the clinician. With gear 92 engaged with teeth 88, rotation of rod 90 rotates rotatable member 87. Thus, rod 90 and gears 88 function much like a worm gear and this configuration can be utilized to rotate section 86 when desired. In some embodiments, a second rod 90a may also be utilized on the opposing side of section 84, and/or a motor may be disposed in or adjacent working channel 82 and be coupled to member 87 for rotating member 87. In alternative embodiments, rotatable member 87 and/or rod 90 may have mating or complementary screw threads (or a screw thread on one structure and a gear on the other to drive the screw thread) that provide essentially the same features.

Rod 90 may utilize any number of different forms and/or material compositions. For example, rod 90 may be made from a metal or metal alloy. Some examples of suitable metals and metal alloys include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material. Alternatively, rod 90 may comprise a polymer, metal-polymer composite, and the like, or any other suitable material.

Section 86 and rotatable member 87 may be desirable for a number of reasons. For example, a clinician may dispose an endoscopic instrument (such as any of those shown or described herein) through channel 82 and then need to rotate the instrument. With a non-circular section of the instrument "keyed" with section 86, a clinician can rotate rod 90 to rotate rotatable member 87 and, consequently, the instrument.

Another desirable feature of rotatable member 87 is that because it may be placed at or near the distal end of channel 82, torque can be applied directly at the distal end of the instrument rather than at the proximal end of the instrument. This may result in a more efficient transfer of torque and it may reduce the incidence of backlash because of the fact that torque is being applied to the instrument at a location that is much closer to where torque transmission is desired (e.g., near the end effector).

FIG. 7 illustrates an alternative section 186 that includes rotatable member 187 that is rotatable within section 84 of channel 82. One or more wires 194 are disposed about rotatable member 187, with ends 192a/192b of wires 194 extending into openings 93 and then extending proximally to a location accessible by the clinician. Ends 192a/192b or wires 194 can be pulled by the clinician in order to rotate section 186. For the same reasons set forth above, this may help to efficiently transmit torque and reduce backlash.

Figure 8:
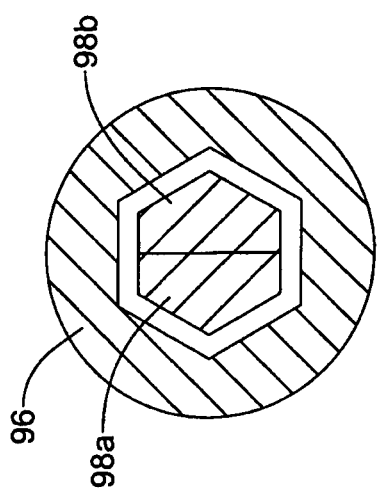
FIG. 8 is a cross-sectional view of another example working channel having a plurality of endoscopic instruments disposed therein.

FIG. 8 illustrates another example working channel 96 that is similar in form and function to the other channels described above. A plurality of instruments 98a/98b are disposed in channel 96. This arrangement demonstrates that multiple instruments 98a/98b, each having a non-circular cross-sectional shape, can be disposed in channel 96. In some embodiments, instruments 98a/98b may have a combined shape that is complementary to the cross-sectional shape of channel 96. The combination of instruments 98a/98b, thus, may take advantage of the desirable features of the "lock-and-key" arrangement described above. Alternatively, a plurality of generally circular instruments 99a/99b may be disposed in channel 96 as shown in FIG. 9. This arrangement may be desirable by reducing the surface area contract between instruments 99a/99b and channel 96 as described above. Of course, a combination of these arrangements is also contemplated where a non-circular instrument (e.g., instrument 98a) and a generally circular instrument (e.g., instrument 99a) are disposed in channel 96. Regardless of what arrangement is utilized, any combination of instruments 98a/98b/99a/99b may be used with any suitable channel, including any of those described herein.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An endoscopic instrument assembly, comprising:
  an endoscope including a lumen, wherein the lumen includes:
    a first portion having a substantially circular cross-sectional shape;
    a second portion having a substantially circular cross-sectional shape; and
    a third portion having a substantially non-circular cross-sectional shape, wherein the third portion is disposed between the first portion and the second portion; and
  a plurality of instruments disposed within the lumen, wherein a combined shape of at least a portion of the plurality of instruments is complementary with the substantially non-circular cross-sectional shape of the third portion;
  wherein the plurality of instruments includes a first instrument and a second instrument that are axially translatable relative to each other.

2. The endoscopic instrument assembly of claim 1, wherein a cross-sectional shape of the plurality of instruments is substantially the same as the non-circular cross-sectional shape of the third portion.

3. The endoscopic instrument assembly of claim 1, wherein the combined shape of the at least a portion of the plurality of instruments includes a portion of the first instrument at a same axial position as a portion of the second instrument.

4. The endoscopic instrument assembly of claim 1, wherein an outer surface of one of the plurality of instruments complements a first section of the substantially non-circular cross-sectional shape, and an outer surface of another of the plurality of instruments complements a second section of the substantially non-circular cross-sectional shape.

5. The endoscopic instrument assembly of claim 1, wherein the third portion of the lumen includes a polygonal cross-sectional shape.

6. The endoscopic instrument assembly of claim 5, wherein the combined shape of the at least a portion of the plurality of instruments includes a polygonal cross-sectional shape.

7. The endoscopic instrument assembly of claim 6, wherein the polygonal cross-sectional shape of the plurality of instruments is substantially the same as the polygonal cross-sectional shape of the third portion.

8. The endoscopic instrument assembly of claim 1, wherein the third portion is rotatable relative to the first portion, and the instrument assembly further comprises a control member for rotating the third portion.

9. The endoscopic instrument assembly of claim 8, wherein the control member includes one or more wires disposed around the third portion.

10. The endoscopic instrument assembly of claim 8, wherein the control member includes a gear engaged with the third portion.

11. An endoscopic instrument assembly, comprising:
  an endoscope including a lumen, wherein the lumen includes: a first portion having a first cross-sectional shape; a second portion having a second cross-sectional shape; and
  a third portion having a third cross-sectional shape different than the first and second cross-sectional shapes; and
  a plurality of instruments disposed within the lumen, wherein a combined shape of at least a portion of the plurality of instruments is complementary with the third cross-sectional shape of the third portion;
  wherein the third portion inhibits rotation of the combined shape relative to the endoscope, and wherein the first portion does not inhibit rotation of the combined shape relative to the endoscope;
  wherein the plurality of instruments includes a first instrument and a second instrument that are axially translatable relative to each other.

12. The endoscopic instrument assembly of claim 11, wherein the first and second portions each includes a substantially circular cross-sectional shape, the third portion includes a substantially polygonal cross-sectional shape, and wherein the third portion is disposed between the first portion and the second portion.

13. The endoscopic instrument assembly of claim 12, wherein the combined shape of the at least a portion of the plurality of instruments includes a substantially polygonal cross-sectional shape that is substantially the same as the substantially polygonal cross-sectional shape of the third portion.

14. An endoscopic instrument assembly, comprising:
  an endoscope including a lumen, wherein the lumen includes:
  a first portion having a first inner perimeter;
  a second portion having a second inner perimeter; and
  a third portion having a third inner perimeter with substantially straight sides, wherein the third inner perimeter is different than the first and second inner perimeters, and the third portion is disposed between the first portion and the second portion; and
  a plurality of instruments disposed within the lumen, wherein a combined shape of at least a portion of the plurality of instruments has an outer perimeter with substantially straight sides;
  wherein the combined shape of the at least a portion of the plurality of instruments includes a portion of a first instrument at a same axial position as a portion of the second instrument;
  wherein the plurality of instruments includes a first instrument and a second instrument that are axially translatable relative to each other.

15. The endoscopic instrument assembly of claim 14, wherein the number of substantially straight sides of the outer perimeter is equal to the number of substantially straight sides of the third inner perimeter of the third portion.

16. The endoscopic instrument assembly of claim 14, wherein the combined shape of the at least a portion of the plurality of instruments includes a shape of the plurality of instruments when the plurality of instruments are joined together.

17. The endoscopic instrument assembly of claim 14, wherein an outer surface of one of the plurality of instruments complements a first section of the third inner perimeter, and an outer surface of another of the plurality of instruments complements a second section of the third inner perimeter.

18. The endoscopic instrument assembly of claim 14, wherein the third portion of the lumen includes a polygonal cross-sectional shape.

19. The endoscopic instrument assembly of claim 18, wherein the combined shape of the at least a portion of the plurality of instruments includes a polygonal cross-sectional shape.

20. The endoscopic instrument assembly of claim 14, wherein the plurality of instruments includes a first instrument and a second instrument, wherein the first instrument includes a first elongate member extending between a control member and an end effector of the first instrument, the second instrument includes a second elongate member extending between a control member and an end effector of the second instrument, and the first elongate member is discrete from the second elongate member.

\* \* \* \* \*